United States Patent [19]

Viglia et al.

[11] 4,248,967
[45] Feb. 3, 1981

[54] ENZYMIC COMPLEXES ADAPTED TO CONVERT RACEMIC HYDANTOINS INTO OPTICALLY ACTIVE AMINOACIDS, AND THEIR APPLICATIONS

[75] Inventors: Aurelio Viglia, Monterotondo; Eugenio Fascetti, Rome; Elena Perricone, Rome; Ludwig Degen, Rome, all of Italy

[73] Assignee: Snamprogetti S.p.A., Milan, Italy

[21] Appl. No.: 885,194

[22] Filed: Mar. 10, 1978

[30] Foreign Application Priority Data

Mar. 15, 1977 [IT] Italy ................................ 21232 A/77

[51] Int. Cl.$^3$ ...................... C12P 13/04; C07B 19/02
[52] U.S. Cl. .................................. 435/106; 435/280;
435/227; 435/832; 435/833
[58] Field of Search .................... 195/2, 29, 62, 65;
435/280, 106–116

[56] References Cited

U.S. PATENT DOCUMENTS

| | | | |
|---|---|---|---|
| 3,964,970 | 6/1976 | Dinelli et al. | 195/2 |
| 4,065,353 | 12/1977 | Cecere et al. | 195/2 |
| 4,094,741 | 6/1978 | Yamada et al. | 195/29 |
| 4,111,749 | 9/1978 | Degen et al. | 195/2 |

*Primary Examiner*—Lionel M. Shapiro
*Attorney, Agent, or Firm*—Morgan, Finnegan, Pine, Foley & Lee

[57] ABSTRACT

Enzymic complexes deriving from micro-organisms belonging to the Bacillaceae family using an hydantoin or a derivative thereof as inductor of the enzymic activity are used for hydrolysing racemic hydantoins into optically active aminoacids. The method of preparation is an enzymic hydrolysis fostered by the enzyme deriving from such special micro-organisms. The hydrolysis can be effected at a comparatively high temperature, which can reach even 60° C.

4 Claims, 1 Drawing Figure

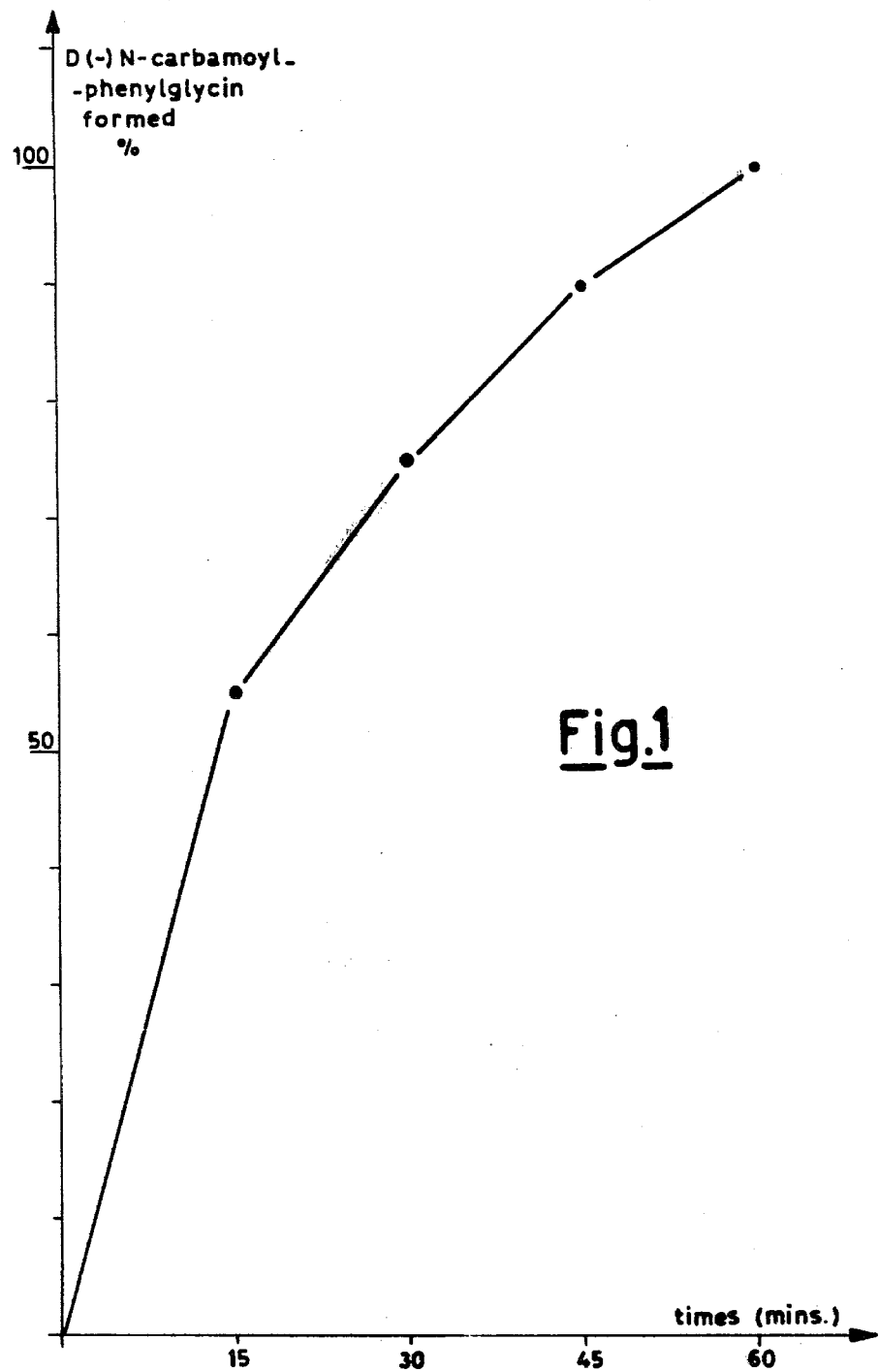

ENZYMIC COMPLEXES ADAPTED TO CONVERT RACEMIC HYDANTOINS INTO OPTICALLY ACTIVE AMINOACIDS, AND THEIR APPLICATIONS

This invention relates to enzymic complexes which are capable of converting racemic hydantoins into optically active aminoacids. More specifically, this invention relates to the hydrolysis of hydantoins into derivatives of aminoacids having the D-configuration. This hydrolysis is conducted by using certain micro-organisms the capacity of which to produce hydropyrimidine hydrolase (E.C.3.5.2.2.) is bound to the presence of hydantoins, as inductors, in the culturing medium. A few aminoacids having the D-configuration, especially phenylglycin and -hydroxyphenylglycin are widely used nowadays as important intermediates in the pharmaceutical industry.

Many attempts have been effected in order to achieve the separation of the optical antiposes: this notwithstanding, none of them has been conducive to any industrially practicable method.

The chemical methods used heretofore for the separation of the optical antiposed are based on the use of optically active compounds, such as camphosulfonic acid, tartaric acid and others.

These, however, have the shortcoming that the conversion yields are low and the running costs are high.

Alternative methods are based on the selective hydrolysis of a D-acyl-aminoacid by the acylase enzyme. However, acylases are comparatively rare and are always polluted by L-acylase, so that a method, which is intricate as itself, is conducive to the obtention of products having a poor optical purity.

The enzymic hydrolysis which is the subject-matter of the present invention, is conducive to the obtention of a simple stereo-isomeric form of an aminoacid, or a derivative thereof, from a racemic compound.

Methods for the enzymic resolution of D,L-aminoacids or their derivatives have already been suggested by the same applicants hereof in the U.S. Pat. No. 3,964,970 dated June 22, 1976 and Application No. 703,966 dated July 9, 1976, now U.S. Pat. No. 4,111,749, issued Sept. 5, 1978.

These prior methods consist in subjecting the racemic form of compounds having the general formula:

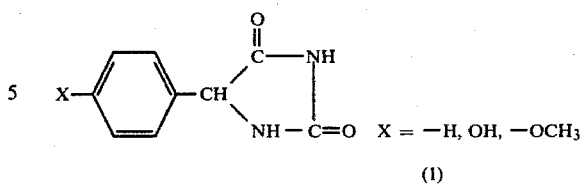

to enzymic hydrolysis, by hydropyrimidine hydrolase extracted from calf liver, or hydropyrimidine hydrolase produced by microorganisms of the Pseudomonas-genus.

Such hydrolysis takes place according to the following chemical reaction pattern:

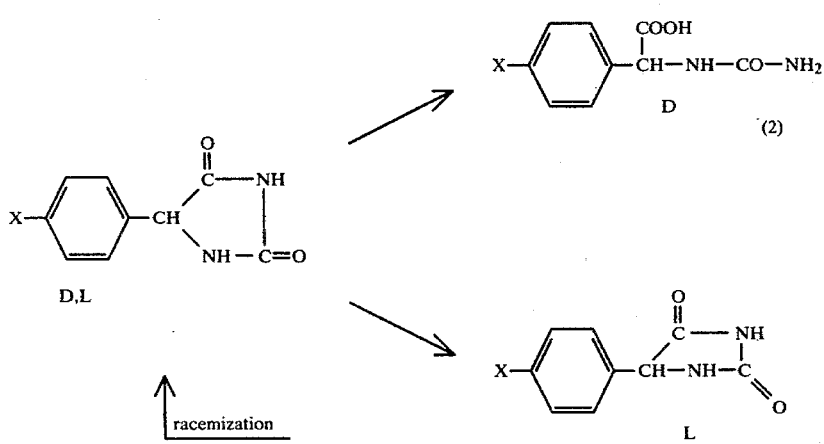

It has now been found that the enzymic resolution of racemic forms of the general formula (1) above, according to the reaction pattern (2) reported above can also be effected with hydrolases which are formed by thermophilic micro-organisms of the *Bacillaceae* family. The hydrolases produced by such microorganisms are heat-resistant and thus they can be used in hydrolytic processes which can be conducted at comparatively high temperatures (40° C. to 60° C.) and permit to operate with solution having a higher concentration of hydantoin, while limiting the drawbacks which are connected with the poor solubility of a few hydantoins at the low and the average temperatures.

According to the present invention, conversely, the cells of the microbial species which belong to the *Bacillaceae* species and which are used for enzymic processes, are cultured under aërobic conditions in culturing media which contain sources of nitrogen and carbon and mineral salts at a temperature comprised between 30° C. and 60° C., preferably between 40° C. and 60° C., for a time from 10 hrs. to 48 hrs. and preferably between 10 hrs. and 24 hrs. and at a pH of from 6 to 8, and preferably from 7.4 to 7.8. As carbon sources there can be used peptone, meat extract, corn steep liquor and, as nitrogen sources, nitrates, as well as ammoniacal salts and hydrolysates of meat, casein and soybean can be used. As inductors of the enzymic activity there are used D,L-hydantoins, preferably the 5,D,L-methyl-hydantoin. The inductor can be added to the culturing medium directly before the sterilization, or during the growth of the micro-organisms.

On comparing the morphological and physiological features of the strains which belong to this invention, with the descriptions reported by the Bergey's Manual, 7th Edition, they belong to the *Bacillaceae* family, genus Bacillus, species *B. brevis, B. stearother mophilus.*

An important modification of the present invention, which still lies within the scope thereof, is given by the fact that the enzyme produced by the strains enumerated above is capable of hydrolyzing the 5-D,L-paramethoxy-phenylhydantoin at a speed which equals that experienced towards 5-D,L-phenylhydantoin, that which is an absolute novelty which is actually unparalleled when compared with that of the hydrolases extracted from other sources.

The method according to the present invention comprises the production of the specific enzyme which is produced during the growth of the micro-organisms and the hydrolysis of hydantoins into derivatives of D-aminoacids with such an enzyme, wherein the enzyme can be directly used as a bacterial suspension or a bacterial culture, or can extracted from the cells.

The test for the selective hydrolysis of the hydantoin derivatives of D,L-aminoacids through micro-organisms was carried into effect as follows:

The bacterial strains, as isolated from earth, compost, vegetables and scraps of various origin, at the temperature of 50° C. were inoculated from slant in 250 ml. Erlenmayer flasks containing 50 mls, each, of the following culturing medium:

Meat peptone: 10 grams per liter
Yeast extract: 10 grams per liter
NaCl: 3 grams per liter
5-D,L-methyl-hydantoin: 1 gram per liter
pH: 7.2
Sterilization for 30 mins at 110° C.

After an incubation of 18–20 hours with orbital stirring at 50° C., there were incubated 500 ml Erlenmayer flasks containing each 100 mls of the same culturing medium with 2 mls of the preculture aforesaid.

After 16 to 18 additional hours, the enzyme reaction was performed with the resting cells, as follows;

Test tubes containing 10 mls of 0.07 molar phosphate buffer of a pH of 8.5 and 20 micromols per milliliter of 5-D,L-phenylhydantoin, were filled with 1 ml of the bacterial suspensions (dry weight 40 milligrams per milliliter).

After a 15 minute incubation at 40° C. the reaction was effected with p-dimethylaminobenzaldehyde for the quantification of the as-formed carbamylderivative (J. Biol. Chem., 238, 3325 (1963)).

TABLE 1 reports the strains which have been used. Of these, there have been deposited, on February 11, 1977, in the Northern Regional Research Center of Peoria, Ill., USA, those connoted by the numbers 1286 and 1287. They have been allotted the following numbers:

NRRL B-11079 for No. 1286, and NRRL B-11080 for No. 1287.

TABLE 1

| Strain | N-carbamylphenylglycin in % of theo. yield |
|---|---|
| 1287 | 60% |
| 1286 | 10% |

It has been seen that while the enzymic hydrolysis of D-hydantoin proceeds at an alkaline pH (pH from 7 to 10), there is, concurrently, the non-enzymic racemization of the remaining L-hydantoin. For this reason, and as a result of the continuous substraction of the D-hydantoin by enzymic hydrolysis, the result at the end of the reaction is all the carbamyl derivative of the D-form. The velocity of racemization of the L-hydantoin is a function of the temperature and the pH and is the higher, the higher the temperature and the pH are. However, by operating at a pH in the surroundings of 8, such a velocity is not so high as to limit the velocity of the reaction of the hydantoinase. The enzymic reaction can be conducted at a temperature comprised between 10° C. and 60° C.: for practical reasons, temperatures ranging from 35° C. to 55° C. are adopted.

The chemical identity of N-carbamylphenylglycin and of N-carbamyl-(paramethoxy)-phenylglycin has been confirmed upon recrystallization of the reaction product on the basis of the IR-spectra, N.M.R. and mass spectrography and elemental analysis.

The optical rotatory powers are, respectively, $[\alpha]_D^{25°}$ C.$= -137°$ (c=1 in 1-normal NH$_4$OH) and $[\alpha]_D^{25°}$ C.$= -140°$ (c=1 in 1-normal NH$_4$OH), which correspond to those reported by the chemical literature.

According to the present invention, the hydrolysis of the hydantoins does not take place exclusively in the presence of micro-organisms in their phases of growth or in the presence of intact cells thereof or the relative spores, but also in the presence of extracts of the micro-organisms aforementioned.

The micro-organisms, for example, can be cultured in a liquid nutrient medium to obtain an accumulation of hydrolase in the cells and the D,L-hydantoins can be added at a subsequent time to the broth-cultures.

The enzymic hydrolysis can also be conducted with the method of the so-called "resting cells". In the latter case, the bacterial cells recovered from the broth-culture and thoroughly washed are slurried in a system which is appropriate and has properly been buffered and the racemic hydantoin is added thereto.

It is likewise possible to use preparations which contain the hydrolase, such as extracts or concentrates thereof, preparations of raw or purified hydrolases and which have been obtained from cells of the above enumerated micro-organisms.

Lastly, a further technical and economical improvement can be achieved by immobilizing the enzyme through combinations thereof with macromolecular compounds via the formation of chemical bonds with the matrix, or via bonds of the ionic type, or by physical immobilization.

The ensuing examples will make conspicuous other operational features which relate to the present invention but do not limit same.

EXAMPLE 1

To 100 mls of a broth-culture of the kind referred to above of the *B.brevis* strain in a 500 ml Erlenmayer flask there were added on the 18th hour of incubation (orbital stirring) at 40° C. 100 mls of phosphate buffer (0.14 molar and pH 8.5) containing 40 micromol per milliliter of 5-(D,L)-phenylhydantoin. After 4 additional hours of incubation under the same conditions, the as-formed N-carbamyl-phenylglycin was determined.

From 705 milligrams of 5-(D,L)-phenylhydantoin there were formed 700 milligrams of N-Carbamyl-phenylglycin, that which corresponds to a yield of 90%, approx.

EXAMPLE 2

Under the same conditions as in Example 1, there were obtained after 4 hours at 40° C. with the strain B.stearothermophilus, from 705 milligrams of 5-(D,L)-phenylhydantoin, 600 milligrams of N-carbamyl-phenylglycin, that which corresponds to a yield of about 85%.

EXAMPLE 3

A culturing medium was prepared which had the composition reported above, containing 1 gram per liter of 5-(D,L)-methylhydantoin. The pH was adjusted to 7.5 with soda and the broth was distributed in 50-ml portions in 250 ml Erlenmayer flasks. Upon sterilization for 30 mins. at 110° C., the flasks were inoculated of the strain of Bacillus brevis from slant containing the same solid medium with agar (DIFCO) at 2% conc. and incubated for 22 hrs. at 40° C. with orbital stirring at 220 rpm.

From such a preculture (Opt. Density at 550 nm=0.4-dilution 1:10) there were inoculated 2 mls in Erlenmeyer flasks of the volume of 500 mls, 100 mls of the same medium and the culture was allowed to be incubated at 40° C. under orbital stirring, 220 rpm, for 18 hours (presporulation phase). The cells separated from the broth by centrifugation at 5,000 g (g for gravity pull) for 20 mins., were washed three times with isotonic solution at a pH of 8.0 and slurried in phosphate buffer of pH 8.5 (0.07 molar) these were the resting cells.

For the reaction of enzymic hydrolysis there were incubated at 40° C. and with orbital stirring (220 rpm) in 250 ml Erlenmayer flasks, 64 mls of the reaction mixture containing 200 milligrams of bacteria (dry weight) and 20 micromols per milliliter of 5-(D,L)-phenylhydantoin (=3.52 milligrams per milliliter). At appropriate time intervals there was measured the product of the hydrolysis, i.e. D-carbamoylphenylglycin, with a colorimetric method at 438 millimicrons. FIG. 1 of the accompanying drawings reports the data in percentage of the theoretical yield of the as-formed carbamoyl derivative, on the abscissae the times in mins. and on the ordinates the percentage of the as-formed D(-)carbamoyl-phenylglycin.

EXAMPLE 4

There were prepared bacterial cells of the B.brevis strain as described in Example 3. A suspension of them (41.5 milligrams per milliliter of dry bacterial cells) in a buffer of phosphate salts, 0.1 molar and pH 8.5, was subjected to mechanical rupturing by the Manton Caulin homogenizer, operating under a pressure of 650 kilograms/square cm at a temperature below 35° C. The cellular debris was removed from the extract by centrifugation (25,000 times the gravity pull for 30 minutes). To 970 mls of buffer of phosphate salts, 0.2 molar, pH 8.5 containing 4.7 grams of 5-(D,L)-phenylhydantoin there were added 30 mls of the extract which contained 280 units of the enzyme. (One unit is the quantity of enzyme which converts 1 micromol per milliliter in one minute of substrate in a phosphate buffer 0.2 molar, pH 8.5 at 50° C., the buffer containing 20 micromol/milliliter of 5-(D,L)-phenylhydantoin). After one hour there were formed 3.2 grams of D-carbamoyl derivative, corresponding to about 63% of the total hydrolysis.

EXAMPLE 5

A semi-synthetic medium was prepared, having the following composition:

| | |
|---|---|
| NH$_4$Cl | 5 grams per liter |
| Na$_2$PO$_4$ | 7.05 grams per liter |
| KH$_2$PO$_4$ | 2.72 grams per liter |
| Meat peptone | 5 grams per liter |
| Yeast extract | 0.5 grams per liter |
| 5-(D,L)-methylhydantoin | 1.0 grams per liter |

The medium was distributed in portions of 50 mls each in Erlenmayer flask of 250 mls of capacity and in portions of 100 mls in Erlenmayer flasks of the capacity of 500 mls and sterilized for 30 mins. at 110° C. The preculture was prepared by inoculating the 250 ml flasks from slant with a culture of the strain B.brevis and incubated as in Example 4, at 40° C. during 22 hours. From this culture (Opt. Density at 550 nm: 0.105, dilution 1:10) there were inoculated 2.5 mls in 500 ml Erlenmayer flasks containing the same medium. After 15 hours of incubation, at 40° C., as above, the resting cells were prepared as in Example 4. The enzymic hydrolysis was carried out at 40° C. in a reaction mixture which contained, in 64 mls of buffer, 100 milligrams of bacteria (referred to the dry weight and equivalent to 100 mls of broth-culture) and 20 micromols per milliliter of 5-(D,L)-phenylhydantoin.

After 5 mins., 10 mins., and 15 mins., there was determined the quantity of the as-formed carbamoyl derivative.

TABLE 2

| Time, mins. | 5 | 10 | 15 |
|---|---|---|---|
| Carbamoyl derivative formed, in micromoles per milliliter | 0.6 | 1.0 | 1.4 |

EXAMPLE 6

A culturing medium was formed, which was constituted exclusively by corn steep liquor, 2.6% (referred to the dry weight) which has not been treated with fresh water (aqua pura). The medium, brought to a pH of 7.5 with KOH was distributed in portions of 50 mls in flasks of 250 mls of capacity, and in portions of 100 mls in 500 ml flasks and sterilized for 30 mins. at 110° C. For the preculture, there were inoculated the 250 ml flasks from slant with a culture of the B.brevis strain and incubated as in Example 4 above at 40° C. for 22 hours.

From this culture were inoculated 2.5 mls in the 500 ml flasks. After 18 hours of incubation at 40° C., as above, the resting cells were prepared as in Example 3. The enzymic hydrolysis was carried out at 40° C., as follows:

(a) in a reaction mixture containing in 64 mls of phosphate buffer (0.07 molar, pH 8.5) the bacterial cells coming from 100 mls of broth-culture and 20 micromols per ml of 5-(D,L)-phenylhydantoin.

(b) in a reaction mixture containing in 64 mls of phosphate buffer (0.07 molar, pH 8.5) the bacterial cells coming from 100 mls of broth-culture and 20 micromol per ml of 5-(D,L)-paramethoxyphenyl hydantoin.

After 5, 10, 15 and 60 mins., the quantity of the as-formed carbamoyl derivative was determined.

TABLE 3

| Time mins. | N-carbamoyl-phenyl-glycin formed, in | | N-carbamoyl-p.methoxy-phenyl-glycin formed, in | |
|---|---|---|---|---|
| | micromols/ml | Conversion % | micromol/ml | Conversion % |
| 5 | 6.55 | 32.8 | 6.45 | 32.3 |
| 10 | 11.1 | 55.5 | 10.9 | 54.5 |
| 15 | 15.05 | 75.5 | 14.85 | 74.2 |
| 60 | 19.8 | 99.0 | 19.85 | 99.2 |

EXAMPLE 7

There was prepared an acetonic powder of the cells of the *Bacillus brevis* strain.

80 milligrams of this powder containing 420 units of the enzyme were suspended in one liter of phosphate salt buffer, 0.2 molar, pH 8.5, containing 5.0 grams of 5-(D,L)-phenylhydantoin. After one hour there had been formed, at a temperature of 50° C. 4.8 grams of D-carbamoyl derivative, corresponding to about 87% of the total hydrolysis.

EXAMPLE 8

A biomass was prepared with the *Bacillus brevis* strain, in a 20-liter Fomel fermentor, containing 16 liters of a culturing medium having the following composition:

| | |
|---|---|
| Yeast extract | 10 grams per liter |
| Meat peptone | 10 grams per liter |
| NaCl | 3 grams per liter |
| $K_2HPO_4$ | 0.56 grams per liter |
| 5-(D,L)-methylhydantoin | 1 gram per liter |
| pH : 7.8 | |
| Sterilization at 110° C. for 30 mins. | |

The culture of the fermentor was inoculated with 160 mls of a preculture (Opt. Dens. at 550 nm: 0.360-dilution 1/10), grown in 500 ml flasks containing 100 mls of the same culturing medium and incubated for 16 hours at 40° C. with orbital stirring at 220 rpm. The fermentation was conducted at 41° C. at a pH of 7.8 by automatic control with double-normal HCl and furnishing to the system an O.A.R. of 0.45. At the 16th hour of fermentation (Opt. Density at 550 nm: 0.350-dilution 1:10), the biomass was separated from the broth by centrifugation in an Alfa-Laval machine at room temperature. On the cells thus obtained and washed with isotonic solution at pH 8.0, there was dosed the enzymic activity. The enzymic hydrolysis was performed at 40° C. (a) in a reaction mixture containing in 64 mls of phosphate salt buffer, 0.07-molar, pH 8.5, 0.5 grams of cellular paste (equivalent to 0.120 grams of dry cells) and 20 micromol per milliliter of 5-(D,L)-hydantoin.

(b) in a reaction mixture as (a) containing 20 micromol/ml of 5-(D,L)-p.methoxyphenylhydantoin.

After 5, 10, 15 and 60 mins. the quantity of the formed carbamoyl derivative was determined.

TABLE 4

| Time mins. | formed N-carbamoylphenyl-glycin | | formed N-carbamoylp.-methoxy phenylglycin | |
|---|---|---|---|---|
| | micromol/ml | % | micromol/ml | % |
| 5 | 4.05 | 20.2 | 4.10 | 20.5 |
| 10 | 7.6 | 38.0 | 7.65 | 38.2 |
| 15 | 10.4 | 52.0 | 10.5 | 52.5 |
| 60 | 18.2 | 91.0 | 18.1 | 90.5 |

We claim:

1. A method for the preparation of N-carbamoyl-phenylglycine which comprises contacting 5-D,L-phenylhydantoin with an enzyme complex derived from *Bacillus brevis*-NRRL-B-11080 at a temperature of from 40°-60° C. until N-carbamoyl-phenylglycine is formed.

2. A method for the preparation of N-carbamoyl-p-methoxyphenylglycine which comprises contacting 5-D,L-paramethoxyphenylhydantoin at a temperature of from 40°-60° C. with an enzyme complex derived from *Bacillus brevis*-NRRL-B-11080 until N-carbamoyl-p-methoxyphenylglycine is formed.

3. A method for the preparation of N-carbamoyl-phenylglycine which comprises contacting 5-D,L-phenylhydantoin at a temperature of from 40°-60° C. with an enzyme complex derived from *Bacillus stearothermophillus*-NRRL-B-11079.

4. A method for the preapartion of N-carbamoyl-p-methoxyphenylglycine which comprises contacting 5-D,L-paramethoxyphenylhydantoin at a temperature of from 40°-60° C. with an enzyme complex derived from *Bacillus stearothermophillus*-NRRL-B-11079.

* * * * *